US011865207B2

(12) United States Patent
De Souza Teixeira et al.

(10) Patent No.: US 11,865,207 B2
(45) Date of Patent: Jan. 9, 2024

(54) TOPICAL PHARMACEUTICAL COMPOSITION FOR TREATMENT OF ANAL FISSURES AND HEMORRHOIDS

(71) Applicant: Ferring B.V., Hoofddorp (NL)

(72) Inventors: Leonardo De Souza Teixeira, São Paulo (BR); Jeane Roberta Santana De Faria, São Paulo (BR); Gílbia De Castro Melo Nogueira, São Paulo (BR); Iram Moreira Mundim, São Paulo (BR); Laura Moreira Rezeck, São Paulo (BR); Carina Pimentel Itapema Alves, São Paulo (BR); Karini Bruno Bellorio, São Paulo (BR); Sarah Rodrigues Fernandes, São Paulo (BR); Viviane Pimentel Itapema Alves, São Paulo (BR); Robert Frederic Wooley De Mendonça Filho, São Paulo (BR)

(73) Assignee: Ferring B.V., Hoofddorp (NL)

( * ) Notice: Subject to any disclaimer, the term of this patent is extended or adjusted under 35 U.S.C. 154(b) by 124 days.

(21) Appl. No.: 17/050,135

(22) PCT Filed: Apr. 25, 2019

(86) PCT No.: PCT/EP2019/060643
§ 371 (c)(1),
(2) Date: Oct. 23, 2020

(87) PCT Pub. No.: WO2019/207059
PCT Pub. Date: Oct. 31, 2019

(65) Prior Publication Data
US 2022/0151918 A1    May 19, 2022

(30) Foreign Application Priority Data
Apr. 25, 2018    (BR) .......................... 1020180083244

(51) Int. Cl.
| | |
|---|---|
| *A61K 31/167* | (2006.01) |
| *A61K 9/00* | (2006.01) |
| *A61K 9/06* | (2006.01) |
| *A61K 31/554* | (2006.01) |
| *A61K 45/06* | (2006.01) |

(52) U.S. Cl.
CPC .............. *A61K 9/0031* (2013.01); *A61K 9/06* (2013.01); *A61K 31/167* (2013.01); *A61K 31/554* (2013.01); *A61K 45/06* (2013.01)

(58) Field of Classification Search
CPC ...... A61K 9/0031; A61K 9/06; A61K 31/167; A61K 31/554; A61K 45/06
See application file for complete search history.

(56) References Cited

U.S. PATENT DOCUMENTS

| | | | | | |
|---|---|---|---|---|---|
| 4,118,480 | A | * | 10/1978 | Williams | ............. A61K 33/245 |
| | | | | | 514/882 |
| 2003/0035850 | A1 | * | 2/2003 | Blanco | ..................... A61K 9/06 |
| | | | | | 514/882 |
| 2003/0114394 | A1 | * | 6/2003 | Levine | ..................... A61P 9/06 |
| | | | | | 514/304 |
| 2008/0317679 | A1 | | 12/2008 | Tamarkin et al. | |
| 2015/0374644 | A1 | | 12/2015 | Hochman | |

FOREIGN PATENT DOCUMENTS

| | | | |
|---|---|---|---|
| CN | 1771981 | A1 * | 10/2005 |
| EP | 0 680 759 | A1 | 11/1995 |
| JP | S61-212515 | | 9/1986 |
| JP | 2006-518711 | | 8/2006 |
| JP | 2008-526932 | | 7/2008 |
| JP | 5030958 | | 9/2012 |
| JP | 2012-527463 | | 11/2012 |
| JP | 2016-517429 | | 6/2016 |
| RO | 126996 | | 1/2012 |
| RO | 126996 | * | 3/2013 |
| WO | WO-98/36733 | A2 | 8/1998 |
| WO | WO-98/36733 | A3 | 11/1998 |
| WO | WO-2005/020960 | | 10/2005 |
| WO | WO-2007/003204 | A1 | 1/2007 |
| WO | WO-2016/118040 | A1 | 7/2016 |
| WO | WO-2017/117268 | A1 | 7/2017 |

OTHER PUBLICATIONS

Carapeti et al., "Topical diltiazem and bethanechol decrease anal sphincter pressure without side effects," Gut, vol. 45, pp. 719-722 (1999).
Database WPI Week 201657 Thomson Scientific, London, GB, AN 2016-46694T, XP002792721 & WO 2016/118040 A1 (Jul. 2016).
Knight et al., "Topical diltiazem ointment in the treatment of chronic anal fissure," British Journal of Surgery, vol. 88, pp. 553-556 (2001).
Sobrado et al., "Tratamento tópico das doenças anorretais" (Topical treatment of anorectal diseases), RBM, vol. 71, No. 1/2, pp. 34-42 (2014).
"Rectal dilator," Wikipedia (Feb. 2019) 1 page, retrieved from the Internet, URL: https://en.wikipedia.org/wiki/Rectal_dilator [retrieved on Jul. 8, 2019].
Office Action issued in Eurasian Application No. 202092546 dated Apr. 27, 2022.
Office Action for European Application No. 19 719 880.7 dated May 19, 2022.

(Continued)

*Primary Examiner* — Ali Soroush
(74) *Attorney, Agent, or Firm* — Foley & Lardner LLP

(57) ABSTRACT

The present invention relates to a topical pharmaceutical composition to be used in the anal region for anal fissures and hemorrhoids, including the postoperative period of hemorrhoidectomy. The pharmaceutical composition comprises an anal dilator, a mucoadhesive polymer and a non-aqueous vehicle. Also described is a method of manufacturing the pharmaceutical composition.

22 Claims, No Drawings

(56) References Cited

OTHER PUBLICATIONS

B. Chatterjee et al. "Mucoadhesive Polymers and Their Mode of Action: A Recent Update" Journal of Applied Pharmaceutical Science vol. 7 (05), pp. 195-203, May 2017.
Office Action issued in Japanese Patent Application No. 2020-560249 dated May 9, 2023.
V. Grabovac et al. "Comparison of the mucoadhesive properties of various polymers" Science Direct; Advanced Drug Delivery Reviews 57 (2005) 1713-1723.
Notice of Reason(s) for Refusal dated Oct. 31, 2023, received in Japanese Patent Application No. 2020-560249.

* cited by examiner

TOPICAL PHARMACEUTICAL COMPOSITION FOR TREATMENT OF ANAL FISSURES AND HEMORRHOIDS

CROSS-REFERENCE TO RELATED APPLICATIONS

The present application is the U.S. National Stage of International Application No. PCT/EP2019/060643, filed Apr. 25, 2019, and claims priority to Brazilian Patent Application No. 1020180083244, filed Apr. 25, 2018.

APPLICATION FIELD

The present invention relates to a topical pharmaceutical composition to be used in the anal region for anal fissures and hemorrhoids, including the postoperative period of hemorrhoidectomy.

DESCRIPTION OF PRIOR ART

Anal fissure is an anorectal disease affecting at least 11% of the world population. This pathology is characterized by a laceration or ulcerated lesion on the skin that lines the anal canal or the margin of the anus and often results in the onset of spasms and bleeding during evacuation. In addition to spasms and bleeding in the anal region, its main symptoms are pain during defecation, pruritus, irritation of the skin in the anal region and rectal prolapse in some patients. This disease also affects men and women of all ages and their most frequent causes are diet, irritable bowel disease, Crohn's disease and local trauma.

Anal fissure treatment commonly involves the application of an anesthetic for pain management, use of therapeutic pads, and waiting for wound healing (which usually occurs within 6 to 8 weeks after the onset of the treatment). In a few cases, depending on the wound severity, the depth of the wound and the hemorrhagic degree, the patient may undergo surgery for wound suture.

Anal fissure is a separate condition from a hemorrhoid, which consists of dilatation of submucosal anorectal veins due to elevated venous pressure in the hemorrhoidal plexus. External hemorrhoids occur below the pectine line and are covered by scaly or cutaneous epithelium. Internal hemorrhoids, on the other hand, are located in the internal hemorrhoidal plexus above the pectine line and are covered by columnar mucosa or transitional epithelium. The main symptoms presented by patients with hemorrhoidal disease are: bleeding, prolapse of the hemorrhoidal nipple, anal pain or discomfort, acute inflammation (thrombosis with or without signs of phlebitis), irritation or perianal dermatitis, and sensation of incomplete rectal emptying post-evacuation.

Typically, the treatment of hemorrhoids involves: changes in the patient's eating habits, adequate hygiene of the region and the use of topical agents such as antiseptics, vasodilators and anesthetics.

Other methods of treatment common to hemorrhoids and anal fissures are described below. The application of topical corticosteroids may reduce local inflammation. This group of drugs, however, has little efficacy in the treatment of the disease (there is no clinical evidence attesting to the reduction of edema, haemorrhage or hemorrhoidal protrusion from the use of these drugs). However, topical corticosteroids have as a side effect the risk of infection and cutaneous atrophy.

Botulinum toxin has already been used experimentally for the treatment of anal fissures. Laboratory studies have identified that its efficacy is similar to the efficacy of nitrate ointments. Although with a lower rate of adverse effects, it presents a lower rate of healing and a greater recurrence than surgical sphincterotomy. The cost of the treatment is high and the dose and technique used are not standardized. Prolonged use of botulinum toxin may lead to infection, local hematoma, hemorrhoidal thrombosis and the possibility of transient incontinence.

Lidocaine, cinchocaine and other amide-type anesthetics have been used topically for symptomatic improvement in patients with anal fissures. Anesthetics of the amide group are more common than other groups of anesthetics for topical application in this region, since they do not cause allergic reactions and sensitization like the ester-type anesthetics that are metabolized into methylparabenzoic acid.

The use of betanechol for treatment of fissures provides a good clinical response, with a low occurrence of complications and side effects. However, in laboratory studies comparing betanechol with diltiazem, it has been found that diltiazem supports a successful clinical response by greater time between and fewer occurrences of relapse in the treatment of anal fissures and hemorrhoids.

Some calcium channel blockers (such as diltiazem and nifedipine) have been used in the treatment of anal fissures and in the postoperative period of hemorrhoidectomy by reducing the resting pressure of the sphincter, facilitating wound healing in the internal region and at the edge of the anal cavity. An article by Dr. Carlos Walter Sobrado of the Faculty of Medicine of the University of São Paulo, Treatment of Anorectal Diseases published in November 2013, states that the use of 2% topical diltiazem in an ointment revealed a healing rate of 75% while topical 0.2% nifedipine has achieved a healing rate of 80% to 90%. E. A. Carapeti, et al. Topical Diltiazem and Bethanechol Decrease Anal Sphincter Pressure Without Side Effects, 1999 discloses the use of diltiazem for topical and oral application in the treatment of anal fissures, revealing a preference for topical use of the substance at 2% concentration.

In general, the aforementioned active agents are available in the form of individualized ointments consisting of a petroleum jelly formulation and additional elements such as Aloe vera, astringents and antiseptics, which often temporarily inhibit the symptoms of the disease, without solving the anal fissure condition in an effective and lasting way.

Petroleum jelly (VASELINE®, petrolatum), as the pharmacological excipient most used in the manufacture of topical preparations for the treatment of anal fissures, brings severe drawbacks to the treatment of fissures, as described further below. Petroleum jelly, despite good spreadability, does not have good adhesion to human skin, often dripping (especially at temperatures above 35° C.), soiling the patient's clothing and not keeping the active ingredients of the drug in contact with human skin for a therapeutically sufficient amount of time.

Moreover, the need for reapplication of creams, ointments, and gels for the treatment of anal fissures and hemorrhoids is a common complaint in the proctologist literature.

When treatment with more than one active ingredient is needed, it is advantageous to have the active in the same formulation for a variety of reasons: (i) when acquiring the different medicines for different active agents, the patient is subjected to the inconvenience of double application of the product in his anal region (an inconvenience that worsens in the same proportion of the sensitivity of the fissures); (ii) when applying the product with distinct active agents, the patient first deposits a layer of the product containing a first active agent on the affected regions, then performs the application of a second layer with a second active agent on the first layer (evidently, in this situation, the active agent of the second layer may see retarded absorption by the human skin due to the presence of the first layer); and (iii) by combining two distinct active agents with conventional excipients, the end user cannot predict the interference of one formula in the other, an active agent interacting with the other formulation, for example.

There remains a need for a topical formulation for use in anal fissures and hemorrhoids that includes at least one active ingredient inhibiting pain and at least one active ingredient for relaxing anal muscle tone, where the two principles are combined in a stable and adequate formulation. Preferably, the formulation would mitigate the inconveniences and inefficiencies of petroleum jelly, such as not dripping after the application, providing greater adhesion to the patient during the treatment and providing stability to the active agents.

OBJECTIVES OF THE INVENTION

The object of the invention is a formulation that allows for the combination of two or more effective drugs for treatment of anal fissures, hemorrhoids and treatment in the anal region. In certain embodiments, the formulation includes functional excipients for spreadability, adhesion and viscosity appropriate to the application of a topical medicament in the anal region. In certain embodiments, the formulation can be effectively applied once daily.

BRIEF DESCRIPTION OF THE INVENTION

It has been discovered that gels overcome some drawbacks of ointment formulations (e.g., those containing components such as liquid and/or solid petroleum jelly). Gels are semi-rigid systems composed of a three-dimensional network with interlacing of particles or macromolecules solvated by the dispersed phase. Gels can be classified into hydrogels when the continuous phase is aqueous and organogels when the continuous phase is an organic solvent.

It has further been discovered that organogels have improved properties over hydrogels with respect to the active agents contemplated in the present invention. It was found that water in the gel formulation could cause undesirable changes such as: (i) the creation of an environment conducive to the proliferation of microorganisms, which rely on water to survive; (ii) direct chemical change in the active agents by reactions such as hydrolysis caused by the medium; and (iii) physical instability of the formulation.

The present invention includes a topical pharmaceutical composition suitable for application to the anal region, which comprises: a local anesthetic for topical use, an anal dilator (together the "active ingredients"), a non-aqueous vehicle, and a mucoadhesive polymer, preferably delivered in a single organogel. In certain embodiments, the anal dilator is the sole active ingredient. The invention also includes a manufacturing process for the topical pharmaceutical composition, which includes the following sequential steps:

Step 1: In a suitable vessel add the non-aqueous vehicle, heat to 20° C. to 50° C.;
Step 2: Add the active ingredient(s) and shake;
Step 3: Cool the solution, if needed, to 20° C. to 40° C. and set aside;
Step 4: Add the polymer, such as a mucoadhesive polymer, together with the non-aqueous vehicle; and Step 5: Optionally add an antioxidant to the product of step 4, shake until complete homogenization.

DETAILED DESCRIPTION OF THE INVENTION

The present invention includes a topical pharmaceutical composition suitable for application to the anal region, said pharmaceutical composition comprising the following elements: a mucoadhesive polymer, optionally a local anesthetic (e.g., for topical use), an anal dilator, and a vehicle. Typically, the vehicle is non-aqueous. By "anal dilator" is meant any vasodilator such as "nitrates and nitrites" (e.g., nitroglycerin/glyceryl trinitrate (GTN), isosorbide dinitrate, isosorbide mononitrate, butyl nitrite, amyl nitrite) and "calcium channel blockers" (e.g., amlodipine, diltiazem, felodipine, isradipine, nicardipine, nifedipine, nisoldipine, verapamil) capable of being applied via topical use, having a local effect on the anal sphincter.

A "non-aqueous vehicle" refers to a component of the formulation which serves to form, dissolve, suspend or mix homogeneously with other ingredients to facilitate its administration or makes it possible to prepare the pharmaceutical form; said component being substantially free of water (e.g., less than 1% v/v, less than 0.5% v/v or even less than 0.1% water). Exemplary compounds for the non-aqueous vehicle include, alone or in combinations: caprylic capric acid triglyceride oil, diethyleneglycol monoethyl ether, medium chain mono-diglyceride, castor oil, polyethylene glycol (PEG, e.g., PEG 400), mineral oil, coconut oil, oleic acid, medium chain triglycerides, caprylocaproyl macrogol-8 glyceride, propylene glycol, glycerin and polyethylene glycol derivatives. A preferred combination of compounds for the vehicle comprises propylene glycol, polyethylene glycol 400, diethylene glycol monoethyl ether and caprylocaproyl macrogol-8 glycerides.

Typically, non-aqueous vehicles used in the formulation of the invention are: Propylene glycol and/or Polyethylene glycol and/or diethyleneglycol monoethyl ether and/or Caprylocaproyl macrogol-8 glyceride, which are often in the proportion of 5.0 to 90.0% w/w, such as 70% to 90% w/w or 80% to 90% w/w. In certain embodiments, the non-aqueous vehicle constitutes 70% to 90% w/w of the total composition, with 10% to 20% w/w (14% to 18% w/w) PEG 400, 25% to 35% w/w (30% to 35% w/w) propylene glycol, 20% to 30% w/w (20% to 25% w/w) diethylene glycol monoethyl ether and 10% to 20% w/w (14% to 18% w/w) caprylocaproyl macrogol-8 glycerides.

More preferably, the present invention consists of an organogel for the treatment of anal fissures and/or hemorrhoids in the anal canal, with a formulation consisting of a mucoadhesive platform, a non-aqueous vehicle, diltiazem hydrochloride as an anal dilator, and lidocaine (e.g., the hydrochloride salt) as a local anesthetic.

An "organogel" is a type of gel composed of a gelling agent dispersed in an organic solvent (e.g., a non-aqueous vehicle).

In one embodiment, diltiazem hydrochloride is the anal dilator, as this calcium channel blocker has proven effective in reducing the resting pressure of the anal sphincter. It has already shown good results in the treatment of chronic anal fissure and in the treatment of hemorrhoids, including in the postoperative period following a hemorrhoidectomy. Studies comparing the use of oral and topical diltiazem on decreasing the maximum anal pressure found that topical was more effective, with fewer side effects and cure rates similar to those found with topical nitroglycerin.

In certain embodiments, diltiazem is present at concentrations of 0.1 to 10%, such as 0.5 to 5%, particularly 1% to 3%, more particularly 1% to 2% (e.g., 1%, 2%).

In certain embodiments, lidocaine Hydrochloride or lidocaine base is the anesthetic.

Typically, the concentrations of the two active agents in the formulation of the invention are: lidocaine hydrochloride or lidocaine base, in the proportion of 0.5% to 5% w/w; and diltiazem hydrochloride in the proportion of 0.1% to 10% w/w. Formulations may also include mucoadhesive polymers: hydroxypropylmethylcellulose and/or sodium alginate and/or hydroxyethylcellulose, and/or hydroxypropylcellulose in the proportion of 0.1% to 10% w/w.

In addition to the combination of the two aforementioned active agents in a single pharmaceutical composition, the invention also provides for the placement of such active agents in the form of a gel having suitable viscosity, spreadability and adhesion, which solves problems encountered in the use of petroleum jelly.

Bioadhesion is an interfacial phenomenon in which two materials, at least one of which is of biological origin, are held together for an extended period of time by interfacial forces. The bond may be between an artificial material and a biological substrate, such as adhesion between a polymer and a biological membrane. Adhesion may be defined as a bond produced by the contact between a pressure sensitive adhesive and a surface.

Mucoadhesion is a property arising from the use of bioadhesive polymers with the ability to bind to biological substrates by binding to the mucosal layer or to the cell membrane. This feature allows the residence time of the preparation at the site of action or absorption to be prolonged, enhancing drug contact with the skin and/or mucosal epithelial barrier. Preferably, mucoadhesive polymers used in the present invention have the ability to increase residence time with both the skin and anal mucosa.

Some examples of mucoadhesive polymers are derivatives of cellulose (e.g., methylcellulose, ethylcellulose, hydroxyethylcellulose, hydroxypropylcellulose, hydroxypropylmethylcellulose, carboxymethylcellulose sodium), carbomers, polyethylene glycols, polycarbophil, polyhydroxyethylmethacrylate, poloxamers, ethylene polyoxides, polyvinylpyrrolidone (povidone), vinyls, polyvinyl alcohol, polyacrylic acid derivatives, pyroxylin, hyaluronic acid, sodium and/or calcium alginate, polysaccharides, acacia, agar, pectin, tragacanth, carrageenan, polypeptides, casein, gelatin, karaya gum, guar gum, xanthan gum, pectin and chitosan. Particularly suitable mucoadhesive polymers include hydroxyethylcellulose, hydroxypropylcellulose, sodium alginate and/or hydroxypropylmethylcellulose.

Hydroxypropylmethylcellulose (HPMC) is a nonionic, cold water soluble, hydrophilic polymer that forms a viscous colloidal solution, practically insoluble in hot water, in chloroform, ethanol (95%) and ether, but soluble in mixtures of ethanol and dichloromethane, mixtures of methanol and dichloromethane and mixtures of water and alcohol. Certain degrees of hydroxypropylmethylcellulose are soluble in aqueous solutions of acetone, mixtures of dichloromethane and propane-2-ol and other organic solvents. HPMC exerts some buffering power and can make systems independent of pH. Of the various types of HPMC, the most widely used to prepare swelling matrix systems are those having a high viscosity grade—HPMC 2208, HPMC 2906 and HPMC 2910, according to the specifications of USP XXV/NF XX.

Hydroxyethylcellulose (HEC) is a nonionic ether obtained from the processing of cellulose pulp or cellulose pulp, soluble in water at room temperature, used as a general purpose thickener. It is biodegradable, physiologically inert and forms a hydrocolloid with various applications in the industry. It is soluble in both hot and cold water, forming clear and uniform solutions. It is practically insoluble in acetone, ethanol (95%), ether, toluene and most other organic solvents. In some polar solvents, such as glycols, hydroxyethylcellulose also dissolves or is partially soluble. Aqueous solutions of HEC are relatively stable at pH 2 to 12, without effectively changing the viscosity. Hydroxyethylcellulose solutions are less stable at pH below 5.0, with hydrolysis occurring. At high pHs, oxidation may occur. Hydroxyethylcellulose is subject to enzymatic degradation, with consequent loss of the viscosity of the solution. Enzymes that catalyze this degradation are produced by many bacteria and fungi present in the environment. Therefore, for prolonged storage of such excipient, an antimicrobial preservative should be added in aqueous solutions. Such a polymer may be used with a wide variety of water-soluble antimicrobial preservatives. However, sodium pentachlorophenate produces an immediate decrease in viscosity when added to HEC solutions.

Hydroxypropylcellulose (HPC) is a non-ionic, partially substituted poly (hydroxypropyl) cellulose ether compatible with cationic surfactants. HPC is very soluble in water below 38° C., forming a clear colloidal solution. In hot water, it is insoluble and precipitates as swollen flakes at a temperature between 40 and 45° C. It is soluble in several polar solvents such as short chain alcohols (ethanol, isopropyl alcohol, etc.) and glycols, such as propylene glycol, but insoluble in glycerol. It is also insoluble in aliphatic hydrocarbons such as oils and aromatic hydrocarbons. It is incompatible with methylparaben and propylparaben.

Typically, hydroxypropylmethylcellulose and/or hydroxyethylcellulose and/or hydroxypropylcellulose are combined in proportions of 0.1 to 10% w/w to provide organogel performance.

Sodium alginate is a further suitable mucoadhesive polymer. Alginate is a linear copolymer composed of α-L-guluronic and β-D-manuronic acids with 1-4 linkages. The material varies widely in terms of its ratio between the manuronic (M) and guluronic (G) residues, as well as its sequence structure and degree of polymerization. In this way, the material can present alternating sequences of MG residues and blocks consisting of two or more residues M or G. Sodium alginate is slightly soluble in water, forming a viscous colloidal solution. It is practically insoluble in alcohol (95%), ether, chloroform, and alcohol/water mixtures in which the ethanol content is greater than 30% by weight. Also, it is practically insoluble in other organic solvents and acidified aqueous solutions in which the pH is less than 3. The characteristics of the gels depend on the ratio M/G and the number of cross-links between the polymer chains. Gels are formed in the presence of divalent cations such as $Ca^{2+}$ or $Mg^{2+}$ and the presence of guluronic residue sequences.

In one example, a formulation of the invention includes 0.5 to 10% w/w of hydroxypropylcellulose (HPC). In another example, sodium alginate and/or hydroxyethylcellulose is present at 0.5 to 10% w/w.

In another embodiment of the invention, a skin healing adjuvant is used in the manufacture of the pharmaceutical composition. Although this element is not essential for the healing of wounds, its use can aid in tissue repair, promoting faster healing with better results. Some examples of skin healing adjuvants are: papain, D-panthenol, propolis, sunflower oil, calcium alginate, grape-seed oil, hyaluronic acid, chamomile or *Calendula officinalis*. In a particular embodiment, the skin healing adjuvant is D-panthenol, for example used in the proportion of 0.5 to 5% w/w.

Formulations of the invention may also include one or more antioxidants. Antioxidants that can be used include: tocopherol in alpha form (0.01 to 1.0% w/w), gamma and beta form (0.01 to 1.0% w/w); ascorbic acid (0.01 to 1.0% w/w); citric acid monohydrate (0.01 to 1.0% w/w), ascorbyl palmitate (0.01 to 1.0% w/w); butylated hydroxytoluene (0.01 to 1.0% w/w); butylated hydroxyanisole (0.01 to 1.0% w/w); erythorbic acid (0.01 to 1.0% w/w); fumaric acid (0.01 to 1.0% w/w); malic acid (0.01 to 1.0% w/w); methionine (0.01 to 1.0% w/w), monothioglycerol (0.01 to 1.0% w/w); metabisulfite and sodium bisulfite (0.01 to 1.0% w/w); propionic acid propylgalate (0.01 to 1.0% w/w); sodium ascorbate (0.01 to 1.0% w/w); sodium formaldehyde sulfoxylate (0.01 to 1.0% w/w); sodium sulfite (0.01 to 1.0% w/w); sodium thiosulfate (0.01 to 1.0% w/w); dioxide sulfur (0.01 to 1.0% w/w); thymol and polyethyleneglycol succinate of vitamin E (0.01 to 1.0% w/w).

The non-aqueous vehicle aims to promote the dissolution and increase of the solubility of a given active and, in certain embodiments, to improve the cutaneous and percutaneous administration of drugs. A mucoadhesive polymer, dispersed in the vehicle in question forms an organogel. An organogel is a specific type of gel in which the polymer swells and retains the organic solvent in a three-dimensional network. In view of this, some of the advantages of using a medicament given in the form of an organogel may be: delivery of the drug in a way directed to the place of action, longer period of action, improvement in cutaneous and percutaneous administration, ease of administration and non-invasive. Another advantage of organogels is that because of the adhesive power of the pharmaceutical form to the skin, it remains for relatively long periods before washing away and the contact typically occurs in a non-irritating way.

Although the active agents of lidocaine hydrochloride (as an anesthetic) and diltiazem (as an anal dilator) are the preferred active agents used by the present invention, other anesthetics and dilators may be used in place of these drugs.

Alternatives for lidocaine include mepivacaine, etidocaine, lidocaine base, prilocaine, bupivacaine, procaine, chlorprocaine, ropivacaine, tetracaine, cocaine, ametocaine and cinchocaine. It is preferable to use the anesthetics of the amide group to anesthetics of the ester group, since the latter are metabolized into methylparabenzoic acid, which may cause a higher incidence of irritation and allergic reactions.

The anal dilator, in place of diltiazem, may be a drug belonging to the families: dihydropyridine (e.g., nifedipine, felodipine, amlodipine, lacidipine), phenylalkylamines (verapamil), benzodiazepines, and tetralol (mebefradil). Some examples of dilators not belonging to the class of calcium channel blockers that could be applied to the present invention are: topical nitrates, muscarinic agonists, agonists and adrenergic antagonists (indoramine).

Further, it is possible to include Aloe vera in the formulation of the invention. This component acts simultaneously as a moisturizer, astringent, emollient, anti-inflammatory agent, analgesic and skin protector against the UV rays, and immunostimulant.

Manufacturing Process:

The manufacturing process of the pharmaceutical composition of the present invention preferably comprises the following sequential steps:

Step 1: In a suitable vessel add the non-aqueous vehicle, heat to 20° C. to 50° C.;

Step 2: Add the active ingredients (e.g., diltiazem and lidocaine hydrochloride) and shake;

Step 3: Cool the solution to between 20° C. and 40° C., if required, and set aside;

Step 4: In another vessel, add the polymer, such as a mucoadhesive polymer, to the non-aqueous vehicle and stir until complete dispersion;

Step 5: Optionally add a healing adjuvant together with the product of step 4;

Step 6: Optionally add an antioxidant to the product of step 5, shake until complete homogenization.

Step 7: Pour the product of step 3 into the product of step 6 and stir until complete homogenization.

A particular composition includes the following components:

| Agents | Amount for 1 gram (g) | % |
| --- | --- | --- |
| Lidocaine hydrochloride | 0.02 | 2.0 |
| Diltiazem hydrochloride | 0.02 | 2.0 |
| Hydroxypropylcellulose | 0.04 | 4.0 |
| Polyethylene glycol 400 | 0.16 | 16.0 |
| Propylene glycol | 0.32 | 32.0 |
| D-panthenol | 0.05 | 5.0 |
| Diethylene glycol monoethyl ether (Transcutol P) | 0.2296 | 22.96 |
| Alpha-tocopherol | 0.0005 | 0.05 |
| Caprylocaproyl macrogol-8 glycerides (Labrasol) | 0.16 | 16.0 |

The invention claimed is:

1. A topical pharmaceutical composition, comprising:
a mucoadhesive polymer comprising one or more selected from sodium alginate, hydroxypropylmethylcellulose, hydroxyethylcellulose, and hydroxypropylcellulose, one or both of diltiazem and diltiazem hydrochloride, and
a topical local anesthetic, formulated in a non-aqueous vehicle,
wherein the composition comprises at least 70% w/w of the non-aqueous vehicle.

2. The pharmaceutical composition according to claim 1, wherein the composition is a semi-solid formulation selected from an ointment, cream, gel, organogel, and colloid.

3. The pharmaceutical composition according to claim 1, wherein the topical local anesthetic is one or more selected from mepivacaine, etidocaine, lidocaine base, lidocaine hydrochloride, prilocaine, bupivacaine, procaine, chlorprocaine, ropivacaine, tetracaine, cocaine, amethocaine and cinchocaine.

4. The pharmaceutical composition according to claim 1, wherein the topical local anesthetic is an amide anesthetic.

5. The pharmaceutical composition according to claim 1, wherein the composition includes 0.5% to 5% w/w lidocaine hydrochloride as the topical local anesthetic.

6. The pharmaceutical composition according to claim 1, wherein the composition includes 0.1% to 10% w/w of the one or both of diltiazem and diltiazem hydrochloride.

7. The pharmaceutical composition according to claim 1, wherein the non-aqueous carrier comprises one or more organic solvents and the topical local anesthetic and the diltiazem and/or diltiazem hydrochloride are solubilized in said one or more organic solvents and the mucoadhesive polymer is dispersed in said one or more organic solvents.

8. The pharmaceutical composition according to claim 1, wherein the mucoadhesive polymer comprises one or more selected from hydroxypropylmethylcellulose, hydroxyethylcellulose, and hydroxypropylcellulose.

9. The pharmaceutical composition according to claim 1, wherein the composition includes 0.5% to 10% w/w of one or more mucoadhesive polymers selected from hydroxypropylmethylcellulose and hydroxyethylcellulose.

10. The pharmaceutical composition according to claim 1, further comprising one or more of a healing adjuvant and an antioxidant.

11. The pharmaceutical composition according to claim 10,
wherein the healing adjuvant is one or more selected from papain, D-panthenol, propolis, sunflower oil, calcium alginate, hyaluronic acid, camomile, grape seed oil, and *Calendula officinalis*; and
the antioxidant is one or more selected from tocopherol in the alpha, gamma and beta form; ascorbic acid; citric acid monohydrate; ascorbyl palmitate; butylated hydroxytoluene; butylated hydroxyanisole; erythorbic acid; fumaric acid; malic acid; methionine; monothioglycerol; metabisulfite and sodium bisulfite; propionic acid; propylgalate; sodium ascorbate; sodium formaldehyde sulfoxylate; sodium sulfite; sodium thiosulphate; sulfur dioxide; thymol; and polyethylene glycol succinate of vitamin E.

12. The pharmaceutical composition according to claim 10, wherein the composition includes one or more of 0.5% to 7% w/w of the healing adjuvant, and 0.01 to 1.0% w/w of the antioxidant.

13. The pharmaceutical composition according to claim 1, wherein the non-aqueous vehicle comprises one or more selected from capryric capric acid triglyceride oil, diethyleneglycol monoethyl ether, medium chain mono- and didiglycerides, castor oil, mineral oil, coconut oil, oleic acid, medium chain triglycerides, caprylocaproyl macrogol-8 glycerides, propylene glycol, glycerin and polyethylene glycol derivatives, and polyethylene glycol.

14. The pharmaceutical composition according to claim 1, wherein the composition includes 70% to 90% w/w of the non-aqueous vehicle.

15. The pharmaceutical composition according to claim 1, wherein the topical local anesthetic is lidocaine hydrochloride; and the non-aqueous vehicle comprises one or more selected from propylene glycol, coconut oil, oleic acid, polyethylene glycol, diethyleneglycol monoethyl ether, glycerin, medium chain triglycerides, and caprylocaproyl macrogol-8 glycerides.

16. A topical pharmaceutical composition, comprising:
a mucoadhesive polymer comprising hydroxypropylcellulose, diltiazem hydrochloride, and lidocaine hydrochloride, formulated in a non-aqueous vehicle comprising propylene glycol, polyethylene glycol, diethyleneglycol monoethyl ether, and one or more caprylocaproyl macrogol-8 glycerides;
wherein the composition comprises at least 70% w/w of the non-aqueous vehicle.

17. The pharmaceutical composition according to claim 16, further comprising panthenol and an antioxidant comprising alpha-tocopherol.

18. The topical pharmaceutical composition of claim 16, comprising:
about 4% w/w hydroxypropylcellulose,
about 2% w/w diltiazem hydrochloride,
about 2% w/w lidocaine hydrochloride,
about 32% w/w propylene glycol,
about 16% w/w polyethylene glycol,
about 23% w/w/diethyleneglycol monoethyl ether, and
about 16% w/w one or more caprylocaproyl macrogol-8 glycerides.

19. The pharmaceutical composition according to claim 18, further comprising about 5% w/w panthenol and about 0.05% w/w of alpha-tocopherol.

20. A method of treating one or more of anal fissures and hemorrhoids, comprising topically applying to an affected region a pharmaceutical composition, comprising:
a mucoadhesive polymer comprising one or more selected from sodium alginate, hydroxypropylmethylcellulose, hydroxyethylcellulose, and hydroxypropylcellulose,
one or both of diltiazem and diltiazem hydrochloride, and
a topical local anesthetic, formulated in a non-aqueous vehicle,
wherein the composition comprises at least 70% w/w of the non-aqueous vehicle.

21. The method of claim 20, wherein, the pharmaceutical composition comprises:
hydroxypropylcellulose as a mucoadhesive polymer;
diltiazem hydrochloride; and
lidocaine hydrochloride as a topical local anesthetic,
wherein the non-aqueous vehicle comprises propylene glycol, polyethylene glycol, diethyleneglycol monoethyl ether, and one or more caprylocaproyl macrogol-8 glycerides.

22. The method of claim 21, wherein:
the hydroxypropylcellulose is present in the pharmaceutical composition in an amount of about 4% w/w;
the diltiazem hydrochloride is present in the pharmaceutical composition in an amount of about 2% w/w;
the lidocaine hydrochloride is present in the pharmaceutical composition in an amount of about 2% w/w;
the propylene glycol is present in the pharmaceutical composition in an amount of about 32% w/w;
the polyethylene glycol is present in the pharmaceutical composition in an amount of about 16% w/w;
the diethyleneglycol monoethyl ether is present in the pharmaceutical composition in an amount of about 23% w/w; and
the one or more caprylocaproyl macrogol-8 glycerides are present in the pharmaceutical composition in an amount of about 16% w/w.

* * * * *

UNITED STATES PATENT AND TRADEMARK OFFICE
CERTIFICATE OF CORRECTION

| | | |
|---|---|---|
| PATENT NO. | : 11,865,207 B2 | Page 1 of 1 |
| APPLICATION NO. | : 17/050135 | |
| DATED | : January 9, 2024 | |
| INVENTOR(S) | : De Souza Teixeira et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 125 days.

Signed and Sealed this
First Day of July, 2025

Coke Morgan Stewart
*Acting Director of the United States Patent and Trademark Office*